(12) United States Patent
Tran et al.

(10) Patent No.: US 8,740,976 B2
(45) Date of Patent: Jun. 3, 2014

(54) TRANSCATHETER PROSTHETIC HEART VALVE DELIVERY SYSTEM WITH FLUSH REPORT

(75) Inventors: Don Tran, Novato, CA (US); Nathan Wiemeyer, Healdsburg, MN (US)

(73) Assignee: Medtronic, Inc., Minneapolis, MN (US)

( * ) Notice: Subject to any disclaimer, the term of this patent is extended or adjusted under 35 U.S.C. 154(b) by 271 days.

(21) Appl. No.: 13/091,938

(22) Filed: Apr. 21, 2011

(65) Prior Publication Data

US 2011/0264199 A1   Oct. 27, 2011

Related U.S. Application Data

(60) Provisional application No. 61/326,386, filed on Apr. 21, 2010.

(51) Int. Cl.
*A61F 2/24* (2006.01)
(52) U.S. Cl.
USPC ........................................................ 623/2.11
(58) Field of Classification Search
USPC .............................. 623/1.11, 1.12, 1.23, 2.11
See application file for complete search history.

(56) References Cited

U.S. PATENT DOCUMENTS

| | | | |
|---|---|---|---|
| 5,683,451 | A | 11/1997 | Lenker et al. |
| 5,824,041 | A | 10/1998 | Lenker et al. |
| 5,906,619 | A | 5/1999 | Olson et al. |
| 5,957,949 | A | 9/1999 | Leonhardt et al. |
| 7,105,016 | B2 | 9/2006 | Shiu et al. |
| 8,403,977 | B2 * | 3/2013 | Case et al. ................... 623/1.11 |
| 2003/0109886 | A1 * | 6/2003 | Keegan et al. ................ 606/108 |
| 2003/0199963 | A1 | 10/2003 | Tower et al. |
| 2005/0137688 | A1 | 6/2005 | Salahieh et al. |
| 2006/0004439 | A1 | 1/2006 | Spenser et al. |
| 2006/0030923 | A1 | 2/2006 | Gunderson |
| 2006/0052867 | A1 | 3/2006 | Revuelta et al. |
| 2006/0229561 | A1 | 10/2006 | Huszar |
| 2006/0259136 | A1 | 11/2006 | Nguyen et al. |
| 2006/0265056 | A1 | 11/2006 | Nguyen et al. |
| 2007/0005131 | A1 | 1/2007 | Taylor |
| 2007/0088431 | A1 | 4/2007 | Bourang et al. |
| 2007/0239266 | A1 | 10/2007 | Birdsall |
| 2007/0239269 | A1 | 10/2007 | Dolan et al. |
| 2008/0065011 | A1 | 3/2008 | Marchand et al. |
| 2008/0082165 | A1 | 4/2008 | Wilson et al. |
| 2008/0147160 | A1 | 6/2008 | Ghione et al. |
| 2008/0147181 | A1 | 6/2008 | Ghione et al. |
| 2008/0188928 | A1 | 8/2008 | Salahieh et al. |

(Continued)

FOREIGN PATENT DOCUMENTS

| | | |
|---|---|---|
| EP | 1 464 303 A2 | 10/2004 |
| GB | 2433700 | 7/2007 |

(Continued)

*Primary Examiner* — Melanie Tyson

(57) ABSTRACT

A delivery system for use with a prosthetic heart valve having a stent frame to which a valve structure is attached includes a shaft assembly including a distal portion and an intermediate portion, and an inner lumen extending through the shaft assembly. The delivery system includes a sheath assembly defining an outer lumen sized to slidably receive the shaft assembly. At least one flush port is formed in the intermediate portion. The at least one flush port is in fluid communication with the inner lumen and the outer lumen. The delivery system is configured to transition from a loaded state in which the sheath assembly encompasses the prosthetic heart valve to a deployed state in which the sheath assembly is withdrawn from the prosthetic heart valve.

18 Claims, 4 Drawing Sheets

(56) References Cited

U.S. PATENT DOCUMENTS

| | | |
|---|---|---|
| 2008/0262590 A1 | 10/2008 | Murray |
| 2009/0018529 A1 | 1/2009 | Hoffman |
| 2009/0069887 A1 | 3/2009 | Righini et al. |
| 2009/0093876 A1 | 4/2009 | Nitzan et al. |
| 2009/0138079 A1 | 5/2009 | Tuval et al. |
| 2009/0171447 A1 | 7/2009 | Von Segesser et al. |
| 2009/0177275 A1 | 7/2009 | Case |
| 2009/0281619 A1 | 11/2009 | Le et al. |
| 2010/0094411 A1 | 4/2010 | Tuval et al. |
| 2010/0121434 A1 | 5/2010 | Paul et al. |

FOREIGN PATENT DOCUMENTS

| | | |
|---|---|---|
| WO | 2008/138584 | 11/2008 |
| WO | 2009/091509 | 7/2009 |
| WO | WO 2010/120671 A1 | 10/2010 |

* cited by examiner

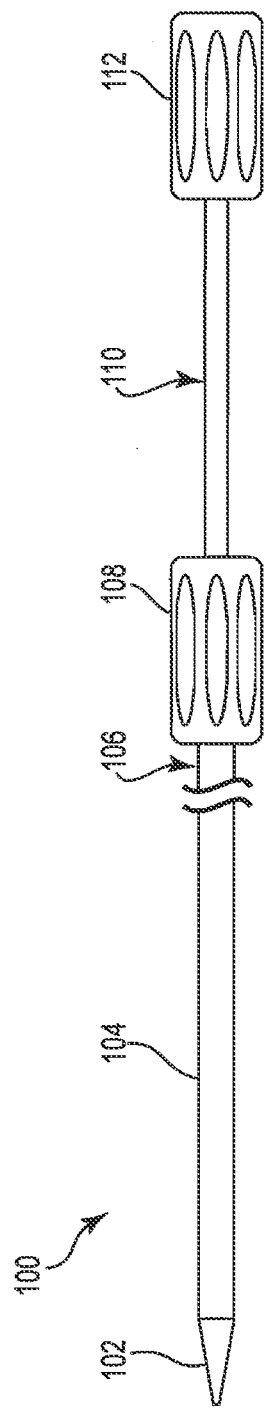
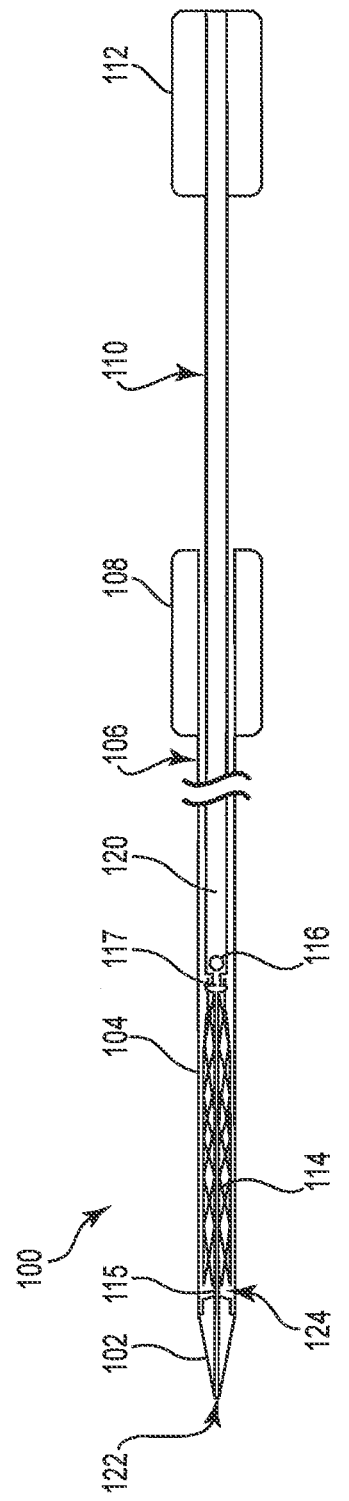

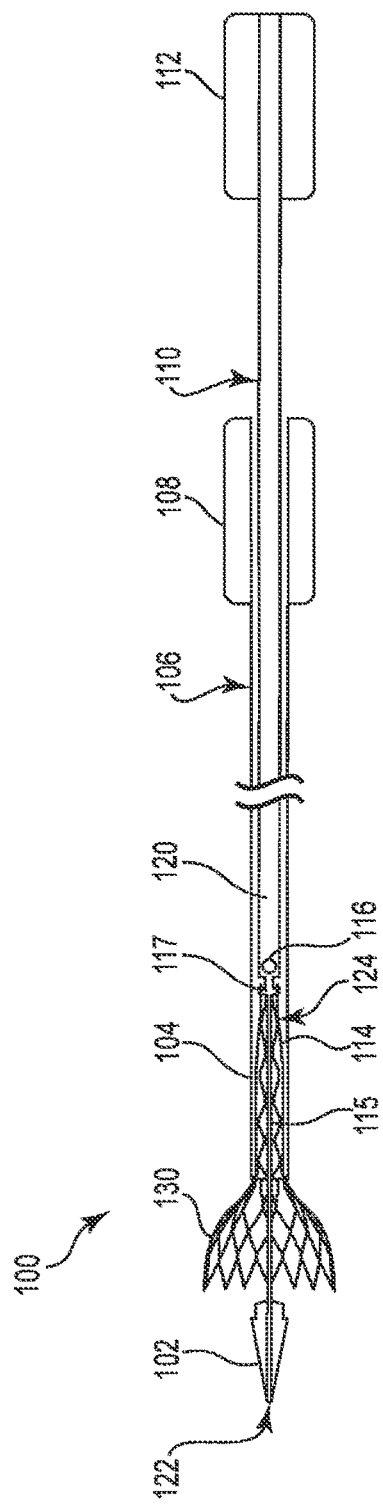

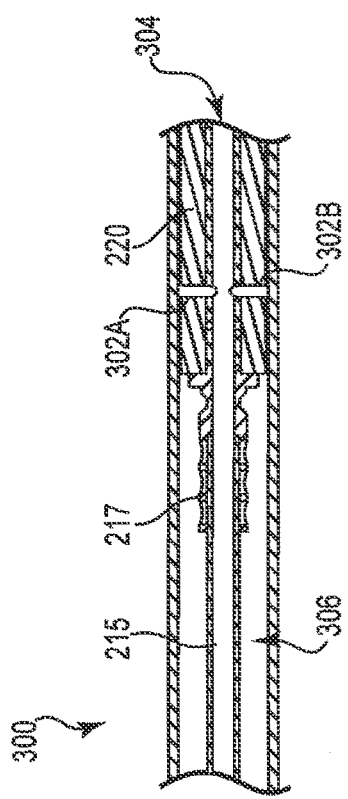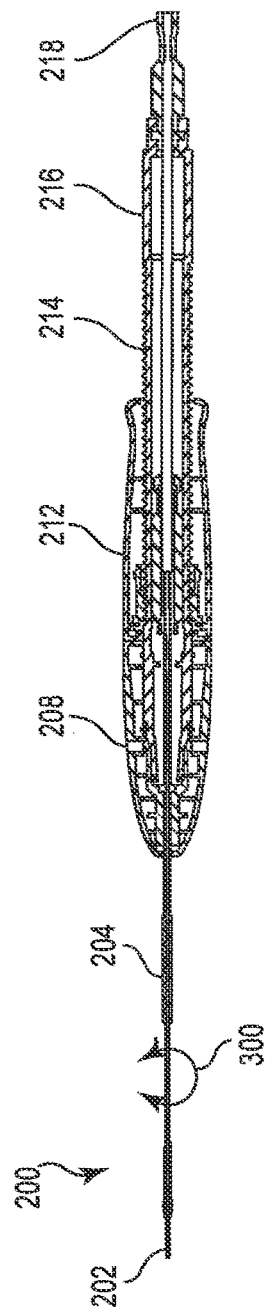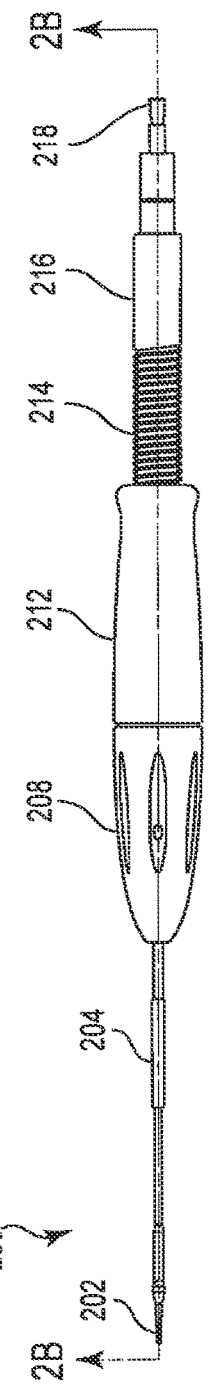

```
┌─────────────────────────────────────────────────────┐
│ RECEIVE A DELIVERY SYSTEM LOADED WITH A SELF-EXPANDING │
│ PROSTHETIC HEART VALVE HAVING A STENT FRAME TO WHICH A │
│ VALVE STRUCTURE IS ATTACHED, WHEREIN THE DELIVERY SYSTEM │
│ INCLUDES A SHAFT ASSEMBLY SLIDABLY POSITIONED WITHIN A │
│ SHEATH ASSEMBLY, THE SHAFT ASSEMBLY INCLUDING A DISTAL │─── 402
│ PORTION, AN INTERMEDIATE PORTION, AND AN INNER LUMEN │
│ EXTENDING THROUGH THE SHAFT ASSEMBLY, THE INTERMEDIATE │
│ PORTION INCLUDING AT LEAST ONE FLUSH PORT FORMED THEREIN, │
│ THE DELIVERY SHEATH DEFINING AN OUTER LUMEN AND │
│ CONTAINING THE PROSTHETIC HEART VALVE IN A COMPRESSED │
│ ARRANGEMENT, THE AT LEAST ONE FLUSH PORT IN FLUID │
│ COMMUNICATION WITH THE INNER LUMEN AND THE OUTER LUMEN │
└─────────────────────────────────────────────────────┘
                          │
                          ▼
┌─────────────────────────────────────────────────────┐
│ FLUIDLY SEAL A DISTAL END OF THE INNER LUMEN         │─── 404
└─────────────────────────────────────────────────────┘
                          │
                          ▼
┌─────────────────────────────────────────────────────┐
│ CONNECT A FLUID SOURCE TO A CONNECTOR AT THE PROXIMAL END │─── 406
│ OF THE INNER LUMEN                                    │
└─────────────────────────────────────────────────────┘
                          │
                          ▼
┌─────────────────────────────────────────────────────┐
│ INTRODUCE FLUID INTO THE INNER LUMEN FROM THE FLUID  │
│ SOURCE WHILE THE DISTAL END IS FLUIDLY SEALED, THEREBY │─── 408
│ SIMULTANEOUSLY FLUSHING THE INNER LUMEN AND THE OUTER │
│ LUMEN                                                 │
└─────────────────────────────────────────────────────┘
```

Fig. 4

TRANSCATHETER PROSTHETIC HEART VALVE DELIVERY SYSTEM WITH FLUSH REPORT

CROSS-REFERENCE TO RELATED APPLICATIONS

This application claims priority under 35 U.S.C. §119(e)(1) to U.S. Provisional Patent Application Ser. No. 61/326,386, filed Apr. 21, 2010, entitled "Transcatheter Prosthetic Heart Valve Delivery System with Flush Port", the entire teachings of which are incorporated herein by reference.

BACKGROUND

The present disclosure relates to systems and methods for percutaneous implantation of a prosthetic heart valve. More particularly, it relates to delivery systems and methods for transcatheter implantation of a stented prosthetic heart valve.

Heart valves, such as the mitral, tricuspid, aortic, and pulmonary valves, are sometimes damaged by disease or by aging, resulting in problems with the proper functioning of the valve. Heart valve problems generally take one of two forms: stenosis in which a valve does not open completely or the opening is too small, resulting in restricted blood flow; or insufficiency in which blood leaks backward across a valve when it should be closed.

Heart valve replacement has become a routine surgical procedure for patients suffering from valve regurgitation or stenotic calcification of the leaflets. Conventionally, the vast majority of valve replacements entail full stenotomy in placing the patient on cardiopulmonary bypass. Traditional open surgery inflicts significant patient trauma and discomfort, requires extensive recuperation times, and may result in life-threatening complications.

To address these concerns, within the last decade, efforts have been made to perform cardiac valve replacements using minimally-invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery of replacement cardiac valves to solve the problems presented by traditional open surgery and minimally-invasive surgical methods. In such methods, a prosthetic heart valve is compacted for delivery in a catheter and then advanced, for example through an opening in the femoral artery and through the descending aorta to the heart, where the prosthetic heart valve is then deployed in the valve annulus (e.g., the aortic valve annulus).

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, prosthetic heart valve designs attempt to replicate the function of the valve being replaced and thus will include valve leaflet-like structures used with either bioprostheses or mechanical heart valve prostheses. If bioprostheses are selected, the replacement valves may include a valved vein segment or pericardial manufactured tissue valve that is mounted in some manner within an expandable stent frame to make a valved stent. In order to prepare such a valve for percutaneous implantation, one type of valved stent can be initially provided in an expanded or uncrimped condition, then crimped or compressed around a balloon portion of a catheter until it is close to the diameter of the catheter. In other percutaneous implantation systems, the stent frame of the valved stent can be made of a self-expanding material. With these systems, the valved stent is crimped down to a desired size and held in that compressed state with a sheath, for example. Retracting the sheath from this valved stent allows the stent to expand to a larger diameter, such as when the valved stent is in a desired position within a patient. With either of these types of percutaneous stent delivery systems, conventional sewing of the prosthetic heart valve to the patient's native tissue is typically not necessary.

Prosthetic heart valve delivery systems may be flushed with a fluid (e.g., saline) to remove air from the system prior to the valve replacement procedure. These systems typically use multiple flushes (e.g., one flush for an inner lumen, and another flush for the regions outside of the inner lumen) with multiple access points or connectors for providing fluid, which can result in a relatively long flushing process.

In light of the above, although there have been advances in percutaneous valve replacement techniques and devices, there is a continued desired to provide different delivery systems for delivering cardiac replacement valves, and in particular self-expanding stented prosthetic heart valves, to an implantation site in a minimally invasive and percutaneous manner, and with improved flushing capabilities.

SUMMARY

One embodiment is directed to a delivery system for use with a prosthetic heart valve having a stent frame to which a valve structure is attached. The delivery system includes a shaft assembly including a distal portion and an intermediate portion, and an inner lumen extending through the shaft assembly. The delivery system includes a sheath assembly defining an outer lumen sized to slidably receive the shaft assembly. At least one flush port is formed in the intermediate portion. The at least one flush port is in fluid communication with the inner lumen and the outer lumen. The delivery system is configured to transition from a loaded state in which the sheath assembly encompasses the prosthetic heart valve to a deployed state in which the sheath assembly is withdrawn from the prosthetic heart valve.

Another embodiment is directed to a system for performing a therapeutic procedure on a defective heart valve of a patient. The system includes a delivery system including a shaft assembly with a distal portion, an intermediate portion, and an inner lumen extending through the shaft assembly. The delivery system includes a sheath assembly defining an outer lumen sized to slidably receive the shaft assembly. At least one flush port is formed in the intermediate portion. The at least one flush port is in fluid communication with the inner lumen and the outer lumen. The system includes a prosthetic heart valve having a stent frame and a valve structure attached to the stent frame and forming at least two valve leaflets. The prosthetic heart valve is self-expandable from a compressed arrangement to a natural arrangement. The delivery system is configured to slidably receive the prosthetic heart valve over the distal portion within the sheath assembly and is configured to be operable to transition from a loaded state in which the sheath assembly encompasses the prosthetic heart valve to a deployed state in which the sheath assembly is withdrawn from the prosthetic heart valve to permit the prosthetic heart valve to self-expand to the natural arrangement and release from the delivery system.

Yet another embodiment is directed to a method of flushing a prosthetic heart valve delivery system. The method includes receiving a delivery system loaded with a self-expanding prosthetic heart valve having a stent frame to which a valve structure is attached. The delivery system includes a shaft assembly slidably positioned within a sheath assembly. The shaft assembly includes a distal portion, an intermediate portion, and an inner lumen extending through the shaft assembly. The intermediate portion includes at least one flush port formed therein. The delivery sheath defines an outer lumen and contains the prosthetic heart valve in a compressed arrangement. The at least one flush port is in fluid communication with the inner lumen and the outer lumen. The method includes fluidly sealing a distal end of the inner lumen, and introducing fluid into the inner lumen while the distal end is fluidly sealed, thereby simultaneously flushing the inner lumen and the outer lumen.

BRIEF DESCRIPTION OF THE DRAWINGS

FIGS. 1A-1C are diagrams illustrating a system for delivering a transcatheter prosthetic heart valve to an implantation site according to one embodiment.

FIGS. 2A and 2B are diagrams illustrating a system for delivering a transcatheter prosthetic heart valve to an implantation site according to another embodiment.

FIG. 3 is a diagram illustrating an expanded view of a region of the delivery system shown in FIG. 2B.

FIG. 4 is a flow diagram illustrating a method of flushing a prosthetic heart valve delivery system according to one embodiment.

DETAILED DESCRIPTION

The terms "distal" and "proximal" are used herein with reference to the treating clinician during the use of the catheter system; "Distal" indicates an apparatus portion distant from, or a direction away from the clinician and "proximal" indicates an apparatus portion near to, or a direction towards the clinician. The term "therapy" or "therapeutic procedure" as used herein in the context of heart valves is intended to include the repair of a heart valve, the replacement of a heart valve, or a combination of repair and replacement of a heart valve. The systems and methods disclosed herein can generally be used for therapy of native or bioprosthetic aortic, mitral, pulmonic, or tricuspid valves.

FIGS. 1A-1C are diagrams illustrating a system 100 for delivering a transcatheter prosthetic heart valve to an implantation site according to one embodiment. System 100 according to one embodiment is configured to be used in performing a therapeutic procedure on a defective heart valve of a patient. In the illustrated embodiment, the system 100 includes a shaft assembly 110 and a sheath assembly 106. The shaft assembly 110 includes a carrier shaft 120 (also referred to as a middle portion or intermediate portion of the shaft assembly 110), a connector shaft 115 (also referred to as a distal portion of the shaft assembly 110), a nose cone 102, and a handle device 112. The connector shaft 115 interconnects the carrier shaft 120 and the nose cone 102, and in some constructions has a reduced-sized outer diameter to permit placement of the stented prosthetic heart valve 114 over the connector shaft 115. In one embodiment, an inner lumen 122 extends through the shaft assembly 110 from a proximal end of the system 100 to a distal end of the system 100.

Carrier shaft 120 is sized to be slidably received within a portion of the sheath assembly 106, and is configured in the illustrated embodiment for releasable coupling with the prosthetic heart valve 114. The carrier shaft 120 forms or includes a coupling device 117. The coupling device 117 is configured to selectively retain a proximal portion of the prosthetic heart valve 114. The coupling device 117 is configured to releasably mount the prosthetic heart valve 114 to the shaft assembly 110 when the prosthetic heart valve 114 is forced to a collapsed state within the sheath assembly 106. In this collapsed state, then, the prosthetic heart valve 114 will longitudinally move with movement of the shaft assembly 110. The sheath assembly 106 is configured to permit deployment of the prosthetic heart valve 114 from the loaded state shown in FIGS. 1A and 1B.

The nose cone 102 can assume a variety of forms, and is generally constructed to facilitate atraumatic placement of the delivery system 100 through a patient's vasculature and heart. The handle device 112 is mounted or connected to a proximal end of the carrier shaft 120, and provides a convenient surface for grasping by a clinician.

The sheath assembly 106 generally includes a sheath 104 and a handle device 108. The sheath 104 can be of a conventional catheter-like configuration (e.g., biocompatible polymer with or without an encapsulated wire braiding). In some constructions, the sheath 104 can further incorporate various steering features. Regardless, the sheath 104 is generally compliant, and is able to traverse the tortuous pathways associated with transcatheter heart valve implantation. The handle device 108 can assume a wide variety of forms, and is generally mounted or connected to a proximal end of the sheath 104. The sheath 104 defines an outer lumen 124 sized to slidably receive the carrier shaft 120, as well as the prosthetic heart valve 114 in the collapsed state.

The delivery system 100 is operable to deliver or implant the prosthetic heart valve 114 as described in further detail below. FIGS. 1A and 1B illustrate the system 100 loaded with the prosthetic heart valve 114 prior to deployment. In particular, the prosthetic heart valve 114 is connected to the carrier shaft 120, for example via the coupling device 117, and is radially constrained within the sheath 104. The delivery system 100 is configured to transition from a loaded state in which the sheath assembly 106 encompasses the prosthetic heart valve 114 to a deployed state in which the sheath assembly 106 is withdrawn from the prosthetic heart valve 114.

The loaded delivery system 100 is advanced toward the implantation target site, for example in a retrograde manner through a cut-down to the femoral artery and into the patient's descending aorta. The delivery system 100 is then advanced, under fluoroscopic guidance, over the aortic arch, through the ascending aorta, and midway across the defective aortic valve (for aortic replacement). After positioning of the delivery system 100, the sheath 104 is partially retracted relative to the prosthetic heart valve 114 as shown in FIG. 1C. For example, the handle device 108 provided with the sheath assembly 106 is retracted toward the handle device 112 of the shaft assembly 110. As shown, a distal region 130 of the prosthetic heart valve 114 is thus exteriorly exposed relative to the sheath 104, and begins to self-deploy. This proximal retraction of the sheath 104 continues, with a continually increasing length of the prosthetic 114 being exposed and thus partially deployed, until the prosthetic 114 is fully deployed at the native heart valve.

The delivery system 100 is useful with a variety of different configurations of a stented heart valve prostheses. In general terms, the prosthetic heart valve 114 includes a stent frame maintaining a valve structure (tissue or synthetic), with the stent frame having a normal, expanded state and collapsible to a collapsed state for loading within the system 100. The stent frame can be constructed to self-deploy or expand when released from the delivery system 100, or a separate expansion member can be provided (e.g., an expansion balloon). For example, the stented heart valve prosthetic heart valve 114 can be a prosthetic sold under the trade name CoreValve® available from Medtronic CoreValve, LLC. Other non-limiting examples of transcatheter heart valve prostheses useful with the system 100 are described in U.S. Publication Nos. 2006/0265056; 2007/0239266; and 2007/0239269; the teachings of each of which are incorporated herein by reference.

As shown in FIGS. 1B and 1C, at least one flush port 116 is formed in the carrier shaft 120 adjacent to the distal end of this shaft 120. The flush port 116 is configured to facilitate flushing of the delivery system 100 with a fluid (e.g., saline), and thereby remove air from the system 100. In one embodiment, inner lumen 122 (e.g., a guide wire lumen, configured to slidably receive a guide wire) is formed through the shafts 115 and 120, and extends from the proximal end of the shaft 120 to the distal end of the shaft 115. The flush port 116 according to one embodiment is in fluid communication with the inner lumen 122 and the outer lumen 124, including the region between an outer diameter of the shafts 115 and 120 and an inner diameter of the sheath 104 (including the space occupied by the prosthetic heart valve 114). Other delivery systems typically use two separate flushes (e.g., one flush for the inner lumen, and another flush for the regions outside of the inner lumen). In contrast, delivery system 100 according to one embodiment is configured to use a single flush for both the inner lumen 122 and the outer lumen 124 using a single access point for introducing fluid into the inner lumen 122, such as by connecting a fluid source (e.g., a syringe) to a connector (e.g., a luer lock-type structure) in the handle 112.

The flushing process according to one embodiment begins by blocking the distal end of the shaft 115 and creating a fluid seal, such as by placing a cap over the distal end of the nose cone 102, inserting a stylet (shipping mandrel) into the distal end of the shaft 115, or blocking the distal end of the shaft 115 with the user's finger. Fluid is then introduced into the inner lumen 122 from the connector in the handle 112. The fluid flows through the inner lumen 122 and the flush port 116 and enters the outer lumen 124, thereby displacing the air in these regions.

FIGS. 2A and 2B are diagrams illustrating a system 200 for delivering a transcatheter prosthetic heart valve to an implantation site according to another embodiment. FIG. 2B illustrates a cross-sectional view taken along section lines 2B-2B in FIG. 2A. FIG. 3 is a diagram illustrating an expanded view of a region 300 of the delivery system 200 shown in FIG. 2B. Delivery system 200 includes a nose cone 202, a sheath 204, a front handle 208, a slider 212, a slide shaft 214, an inner shaft 215, a rear grip 216, a coupling device 217, a connector 218, a carrier shaft 220, and flush ports 302A and 302B (collectively referred to as flush ports 302).

The connector shaft 215 interconnects the carrier shaft 220 and the nose cone 202, and in some constructions has a reduced-sized diameter to permit placement of the prosthetic heart valve over the connector shaft 215. Carrier shaft 220 is sized to be slidably received within the sheath 204, and is configured in the illustrated embodiment for releasable coupling with a prosthetic heart valve. The sheath 204 defines an outer lumen 306 sized to slidably receive the carrier shaft 220, as well as a prosthetic heart valve in a collapsed state. The carrier shaft 220 forms or includes a coupling device 217. The coupling device 217 is configured to selectively retain a proximal portion of the prosthetic heart valve. The coupling device 217 is configured to releasably mount the prosthetic heart valve to the carrier shaft 220 when the prosthetic heart valve is forced to a collapsed state within the sheath 204.

Slider 212 is selectively engaged and disengaged with a threaded outer surface of slide shaft 214 by an actuation button (not shown). When engaged with the threaded outer surface of slide shaft 214, axial rotation of slider 204 is converted into axial translation. Slider 212 is coupled to sheath 204 so that axial translation of the slider 212 in the proximal direction causes a retraction of the sheath 204 relative to the prosthetic heart valve. When disengaged from the threaded outer surface of the slide shaft 214, slider 212 is slidably mounted on slide shaft 214. By sliding slider 212 in the proximal direction, sheath 204 is easily and quickly retracted to rapidly complete deployment of the prosthetic heart valve at the native heart valve.

As shown in FIG. 3, flush ports 302A and 302B are formed in the carrier shaft 220 adjacent to the distal end of this shaft 220. The flush ports 302 are configured to facilitate flushing of the delivery system 200 with a fluid (e.g., saline), and thereby remove air from the system 200. In one embodiment, an inner lumen 304 (e.g., a guide wire lumen configured to slidably receive a guide wire) is formed through the shafts 215 and 220, and extends from the proximal end of the delivery system 200 to the distal end of the delivery system 200. The flush ports 302 according to one embodiment are in fluid communication with the inner lumen 304 and the outer lumen 306, including the region between an outer diameter of the shafts 215 and 220 and an inner diameter of the sheath 204 (including the space occupied by the prosthetic heart valve). Delivery system 200 according to one embodiment is configured to use a single flush for both the inner lumen 304 and outer lumen 306 using a single access point for introducing fluid into the inner lumen 304, such as by connecting a fluid source (e.g., a syringe) to connector 218 (e.g., a luer lock-type structure) at the proximal end of the system 200. The connector 218 is in fluid communication with the inner lumen 304.

The flushing process according to one embodiment begins by blocking the distal end of the shaft 215 and creating a fluid seal, such as by placing a cap over the distal end of the nose cone 202, inserting a stylet (shipping mandrel) into the distal end of the shaft 215, or blocking the distal end of the shaft 215 with the user's finger. Fluid is then introduced into the inner lumen 304 from the connector 218. The fluid flows through the inner lumen 304 and the flush ports 302 and enters the outer lumen 306, thereby displacing the air in these regions.

FIG. 4 is a flow diagram illustrating a method 400 of flushing a prosthetic heart valve delivery system according to one embodiment. At 402, a delivery system loaded with a self-expanding prosthetic heart valve having a stent frame to which a valve structure is attached is received, wherein the delivery system includes a shaft assembly slidably positioned within a sheath assembly, the shaft assembly including a distal portion, an intermediate portion, and an inner lumen extending through the shaft assembly, the intermediate portion including at least one flush port formed therein, the delivery sheath defining an outer lumen and containing the prosthetic heart valve in a compressed arrangement, the at least one flush port in fluid communication with the inner lumen and the outer lumen. At 404, a distal end of the inner lumen is fluidly sealed. At 406, a fluid source is connected to a connector at a proximal end of the inner lumen. At 408, fluid is introduced into the inner lumen from the fluid source while the distal end is fluidly sealed, thereby simultaneously flushing the inner lumen and the outer lumen.

Benefits provided by embodiments described herein include at least the following: (1) A reduction in the size of the gap between the shaft 120 (or 220) and the sheath 104 (or 204), which minimizes the catheter slack effect, helps to increase the deployment accuracy, and reduces the traveling distance at the handle before the sheath starts to respond; (2) a simple, easy, and fast catheter flushing procedure; and (3) cost reduction—one single luer for flushing both the inner lumen and regions outside of the inner lumen.

A test unit was built according to the disclosure herein to evaluate the flushability and deployment response at the catheter handle, and the results were compared to a control unit. The test unit used a carrier shaft 120 (middle member) with a 0.129" outside diameter, and the control unit used a carrier shaft with a 0.125" outside diameter. The test unit was built with two 0.010" diameter flush ports, and a 0.035" stainless steel mandrel was inserted into the distal end of the shaft 115 during the flush. The test results showed that even with a narrower gap clearance between the shaft 120 and the sheath 104, the fluid flow rate (for flushing) for the test unit was superior to the control unit (required 4.5 seconds versus 25.5 seconds to empty 10 cc of water using a 10 cc syringe for testing). Handle travel distance (response delay) of the test unit was also superior (approximately 10 mm vs. 19 mm for the control unit).

Although the present disclosure has been described with reference to preferred embodiments, workers skilled in the art will recognize that changes can be made in form and detail without departing from the spirit and scope of the present disclosure.

What is claimed is:

1. A delivery system for use with a prosthetic heart valve having a stent frame to which a valve structure is attached, the system comprising:
   a shaft assembly including a distal portion and an intermediate portion, and an inner lumen extending through the shaft assembly;
   a sheath assembly defining an outer lumen sized to slidably receive the shaft assembly;
   at least one flush port formed through multiple shafts in the intermediate portion, the at least one flush port in fluid communication with the inner lumen and the outer lumen; and
   wherein the delivery system is configured to transition from a loaded state in which the sheath assembly encompasses the prosthetic heart valve to a deployed state in which the sheath assembly is withdrawn from the prosthetic heart valve.

2. The delivery system of claim 1, wherein the at least one flush port is formed adjacent to a distal end of the intermediate portion.

3. The delivery system of claim 1, and further comprising:
   a connector in fluid communication with the inner lumen, the connector configured to be connected to a fluid source.

4. The delivery system of claim 3, wherein the connector is formed at a proximal end of the delivery system.

5. The delivery system of claim 1, wherein a distal end of the distal portion is configured to be fluidly sealed.

6. The delivery system of claim 5, wherein sealing of the distal end of the distal portion facilitates a flow of fluid from the inner lumen through the at least one flush port and into the outer lumen.

7. The delivery system of claim 1, wherein the intermediate portion has a larger outer diameter than the distal portion.

8. The delivery system of claim 7, wherein the prosthetic heart valve is configured to be slid over the distal portion and releasably attached to the intermediate portion.

9. The delivery system of claim 1, wherein the inner lumen is a guide wire lumen configured to slidably receive a guide wire.

10. A system for performing a therapeutic procedure on a defective heart valve of a patient, the system comprising:
    a delivery system including:
    a shaft assembly including a distal portion, an intermediate portion, and an inner lumen extending through the shaft assembly;
    a sheath assembly defining an outer lumen sized to slidably receive the shaft assembly; and
    at least one flush port formed in the intermediate portion, the at least one flush port extending through multiple shafts and in fluid communication with the inner lumen and the outer lumen;
    a prosthetic heart valve having a stent frame and a valve structure attached to the stent frame and forming at least two valve leaflets, the prosthetic heart valve being self-expandable from a compressed arrangement to a natural arrangement; and
    wherein the delivery system is configured to slidably receive the prosthetic heart valve over the distal portion within the sheath assembly and is configured to be operable to transition from a loaded state in which the sheath assembly encompasses the prosthetic heart valve to a deployed state in which the sheath assembly is withdrawn from the prosthetic heart valve to permit the prosthetic heart valve to self-expand to the natural arrangement and release from the delivery system.

11. The system of claim 10, wherein the at least one flush port is formed adjacent to a distal end of the intermediate portion.

12. The system of claim 10, and further comprising:
    a connector in fluid communication with the inner lumen, the connector configured to be connected to a fluid source.

13. The system of claim 12, wherein the connector is formed at a proximal end of the delivery system.

14. The system of claim 10, wherein a distal end of the distal portion is configured to be fluidly sealed.

15. The system of claim 14, wherein sealing of the distal end of the distal portion facilitates a flow of fluid from the inner lumen through the at least one flush port and into the outer lumen.

16. The system of claim 10, wherein the intermediate portion has a larger outer diameter than the distal portion.

17. The system of claim 16, wherein the prosthetic heart valve is configured to be slid over the distal portion and releasably attached to the intermediate portion.

18. The system of claim 10, wherein the inner lumen is a guide wire lumen configured to slidably receive a guide wire.

* * * * *